United States Patent
Tanabe (10) Patent No.: US 8,657,751 B2
(45) Date of Patent: Feb. 25, 2014

(54) ULTRASOUND DIAGNOSTIC APPARATUS AND ULTRASOUND IMAGE PRODUCING METHOD

(75) Inventor: Tsuyoshi Tanabe, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 108 days.

(21) Appl. No.: 13/396,133

(22) Filed: Feb. 14, 2012

(65) Prior Publication Data

US 2012/0238878 A1    Sep. 20, 2012

(30) Foreign Application Priority Data

Mar. 18, 2011  (JP) .................................. 2011-060744

(51) Int. Cl.
*A61B 8/00*    (2006.01)

(52) U.S. Cl.
USPC ........... 600/447; 600/444; 600/445; 600/437; 600/407

(58) Field of Classification Search
USPC .................................. 600/407, 437, 444–449
See application file for complete search history.

(56) References Cited

U.S. PATENT DOCUMENTS

| 6,210,335 B1 * | 4/2001 | Miller ........................... 600/454 |
| 2004/0073113 A1 * | 4/2004 | Salgo et al. ................... 600/438 |
| 2008/0146932 A1 * | 6/2008 | Chalana et al. ............... 600/447 |

FOREIGN PATENT DOCUMENTS

JP    2009-240525    10/2009

* cited by examiner

*Primary Examiner* — Tse Chen
*Assistant Examiner* — Joel F Brutus
(74) *Attorney, Agent, or Firm* — Young & Thompson (57) ABSTRACT

An ultrasound diagnostic apparatus includes a transmission and reception circuit which electronically scans with a transducer array in an ultrasound probe for acquiring two-dimensional image data; an image producer which produces a three-dimensional ultrasound image using the acquired two-dimensional image data while mechanically scanning with the transducer array in a direction substantially orthogonal to the array direction of the transducer array; and a controller which, when the internal temperature of the ultrasound probe is equal to or higher than a first set value, controls the transmission and reception circuit such that a composite scan including two different electronic scans is performed.

8 Claims, 7 Drawing Sheets

T1 ≦ Tp    TEMPERATURE RISE SUPPRESSION TYPE SCAN B1
IN FORWARD MOVEMENT

T2 ≦ Tp   TEMPERATURE RISE SUPPRESSION TYPE SCAN C
IN FORWARD MOVEMENT

ULTRASOUND DIAGNOSTIC APPARATUS AND ULTRASOUND IMAGE PRODUCING METHOD

BACKGROUND OF THE INVENTION

The present invention relates to an ultrasound diagnostic apparatus and an ultrasound image producing apparatus and particularly to an ultrasonic diagnostic apparatus for producing a three-dimensional ultrasonic image by causing a transducer array to combine an electronic scan and a mechanical scan.

BACKGROUND ART

Conventionally, ultrasound diagnostic apparatus using ultrasound images are employed in medicine. In general, this type of ultrasound diagnostic apparatus comprises an ultrasound probe having a built-in transducer array and an apparatus body connected to the ultrasound probe. The ultrasound probe transmits ultrasonic waves toward a subject, receives ultrasonic echoes from the subject, and the apparatus body electrically processes the reception signals to generate an ultrasound image.

A type of transducer array widely used has ultrasound transducers arrayed one-dimensionally. This type of transducer array is capable of obtaining a two-dimensional tomographic image by electric scan. To view an image in front of or behind the tomographic image, i.e., an image closer to or farther from the viewer in the direction perpendicular to the tomographic image, the position and/or the angle of the ultrasound probe is changed to produce a different tomographic image. Depending on, for example, the shape and the size of the site under examination, a number of two-dimensional tomographic images must be produced to know the state of the site under examination, and, in addition, discomfort may be caused to the patient as the ultrasound probe is moved.

JP 2009-240525 A, for example, describes an ultrasound diagnostic apparatus in which a transducer array performs electronic scan to acquire two-dimensional image data as it performs mechanical scan in a direction substantially perpendicular to its array direction thereby to produce a three-dimensional ultrasound image. The ultrasound diagnostic apparatus enables production of a three-dimensional image without moving the ultrasound probe.

SUMMARY OF THE INVENTION

However, in the ultrasound probe of such ultrasound diagnostic apparatus, the housing of the probe contains a scan mechanism for allowing the transducer array to perform mechanical scan, so that not only the examination for diagnosis causes generation of heat in the transducer array, but the scan mechanism also generates heat, possibly increasing the temperature inside the housing of the ultrasound prob.

In particular, where an ultrasound diagnostic apparatus has an ultrasound probe with a built-in signal processing circuit board to digitally process a reception signal outputted from the transducer array before transmitting the reception signal to the apparatus body via wireless or wired communication thereby to reduce the effects of noise and obtain a high-quality ultrasound image, the circuit board also generates heat and encourages temperature rise in the housing. Temperature rise inside the housing of the ultrasound probe makes it difficult to assure stable operation of the circuits housed therein.

An object of the present invention is to eliminate the above problems associated with the prior art and provide an ultrasound diagnostic apparatus and an ultrasound image producing method enabling acquisition of a high-quality three-dimensional ultrasound image while suppressing the temperature rise inside the ultrasound probe.

An ultrasound diagnostic apparatus according to the invention comprises:

an ultrasound probe which has a one-dimensional array type transducer array and an array moving unit moving the transducer array in a direction substantially perpendicular to an array direction of the transducer array;

a transmission and reception circuit which electronically scans with the transducer array, and transmits and receives an ultrasound beam toward a subject to acquire two-dimensional image data;

an image producer which produces a three-dimensional ultrasound image using two-dimensional image data acquired by the transmission and reception circuit while mechanically scanning with the transducer array in a direction substantially orthogonal to the array direction of the transducer array by the array moving unit;

a region of interest setter which sets a region of interest in an imaging region;

a temperature sensor which detects an internal temperature of the ultrasound probe; and a controller which, when the internal temperature of the ultrasound probe detected by the temperature sensor is equal to or higher than a first set value, controls the transmission and reception circuit such that a composite scan including two different electronic scans is performed, at least one of the two different electronic scans being a temperature rise suppression type scan in which the transmission and reception of ultrasonic beams for at least a part of a region other than the region of interest set by the region of interest setting unit are paused for a longer time period than those when the internal temperature of the ultrasound probe detected by the temperature sensor is below the first set value.

A method of producing an ultrasound image according to the invention comprises the steps of:

setting a region of interest in an imaging region;

detecting an internal temperature of an ultrasound probe;

electronically scanning with a one-dimensional array type transducer array of the ultrasound probe by a transmission and reception circuit and transmitting and receiving ultrasonic beams toward a subject to acquire two-dimensional image data, and mechanically scanning with the transducer array in a direction substantially orthogonal to the array direction of the transducer array to acquire a plurality of pieces of two-dimensional image data;

producing a three-dimensional ultrasound image using a plurality of pieces of acquired two-dimensional image data; and when the detected internal temperature of the ultrasound probe is equal to or higher than a first set value, controlling the transmission and reception circuit such that a composite scan including two different electronic scans is performed, wherein at least one of the two different electronic scans is a temperature rise suppression type scan in which the transmission and reception of ultrasonic beams for at least a part of a region other than the region of interest set are paused for a longer time period than those when the detected internal temperature of the ultrasound probe is below the first set value.

DETAILED DESCRIPTION OF THE INVENTION

Embodiments of the present invention will now be described below based on the appended drawings.

Embodiment 1

Figure 1:
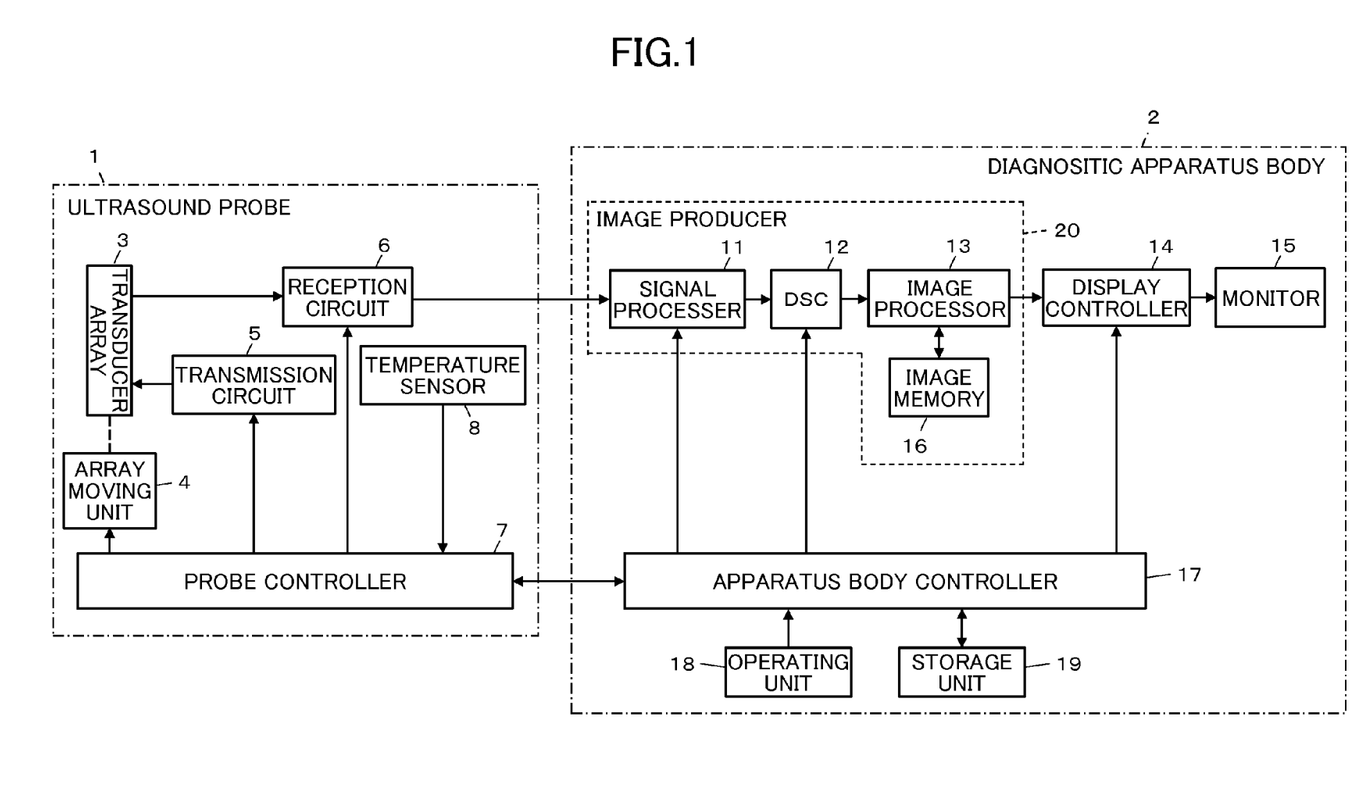
FIG. 1 is a block diagram illustrating a configuration of an ultrasound diagnostic apparatus according to Embodiment 1 of the invention.

FIG. 1 illustrates a configuration of the ultrasound diagnostic apparatus according to Embodiment 1 of the invention. The ultrasound diagnostic apparatus comprises an ultrasound probe 1 and a diagnostic apparatus body 2 connected to the ultrasound probe 1.

The ultrasound probe 1 comprises a transducer array 3 where plural ultrasound transducers are arrayed one-dimensionally. The transducer array 3 is connected to an array moving unit 4, a transmission circuit 5, and a reception circuit 6. The array moving unit 4, the transmission circuit 5, and the reception circuit 6 are connected to a probe controller 7. The ultrasound probe 1 has a built-in temperature sensor 8 connected to the probe controller 7; the temperature sensor 8 detects the temperature inside the ultrasound probe 1. The temperature sensor 8 is located, for example, near the reception circuit 6, where heat is expected to develop particularly during the operation of the ultrasound diagnostic apparatus.

The diagnostic apparatus body 2 comprises a signal processor 11 connected to the reception circuit 6 of the ultrasound probe 1. The signal processor 11 is connected in sequence to a DSC (Digital Scan Converter) 12, an image processor 13, a display controller 14, and a monitor 15. The image processor 13 is connected to an image memory 16. The signal processor 11, the DSC 12, and the display controller 14 are connected to the apparatus body controller 17. The apparatus body controller 17 is connected to an operating unit 18 and a storage unit 19.

The probe controller 7 of the ultrasound probe 1 and the apparatus body controller 17 of the diagnostic apparatus body 2 are connected to each other.

The transducer array 3 of the ultrasound probe 1 comprises a plurality of ultrasound transducers arranged one-dimensionally. Each of the ultrasound transducers comprises a vibrator composed of a piezoelectric body and electrodes each provided on both ends of the piezoelectric body. The piezoelectric body is composed of, for example, a piezoelectric ceramic typified by a PZT (titanate zirconate lead), a polymeric piezoelectric device typified by PVDF (polyvinylidene flouride), or a piezoelectric monochristal typified by PMN-PT (lead magnesium niobate lead titanate solid solution).

When the electrodes of each of the vibrators are supplied with a pulsed voltage or a continuous-wave voltage, the piezoelectric body expands and contracts to cause the vibrator to produce pulsed or continuous ultrasonic waves. These ultrasonic waves are combined to form an ultrasonic beam. Upon reception of propagating ultrasonic waves, each vibrator expands and contracts to produce an electric signal, which is then outputted as reception signal of the ultrasonic waves.

The ultrasound transducers of the transducer array 3 are arranged so as to be able to vibrate or slide substantially perpendicularly to their array direction. The ultrasound transducers are actuated by the array moving unit 4 to repeatedly vibrate with a given period and within a given angular range or linearly reciprocate with a given period and stroke. The array moving unit 4 may be, for example, any of a variety of motors and actuators.

The transmission circuit 5 includes, for example, a plurality of pulsars and adjusts the delay amounts for actuation signals based on a transmission delay pattern selected according to a control signal transmitted from the probe controller 7 so that the ultrasonic waves transmitted from a plurality of ultrasound transducers of the transducer array 3 form an ultrasonic beam, and supplies the ultrasound transducers with delay-adjusted actuation signals.

The reception circuit 6 amplifies and A/D-converts the reception signals transmitted from the ultrasound transducers of the transducer array 3, and then performs reception focusing processing by providing the reception signals with respective delays according to the sonic speed or sonic speed distribution that is set based on a reception delay pattern selected according to the control signal transmitted from the probe controller 7 and adding up the reception signals. This reception focusing processing yields reception data (sound ray signals) having the ultrasonic echoes well focused.

The transmission and reception circuits of the invention are constituted by the transmission circuit 5 and the reception circuit 6.

The temperature sensor 8 detects and outputs an internal temperature Tp of the ultrasound probe 1 to the probe controller 7.

The probe controller 7 controls various components of the ultrasound probe 1 according to control signals transmitted from the apparatus body controller 17 of the diagnostic apparatus body 2.

The signal processor 11 of the diagnostic apparatus body 2 corrects attenuation in the reception data produced by the reception circuit 6 of the ultrasound probe 1 according to the distance, i.e., the depth at which the ultrasonic waves are reflected, and then performs envelope detection processing to produce a B mode image signal, which is tomographic image information on a tissue inside the subject's body.

The DSC 12 converts the B mode image signal produced by the signal processor 11 into an image signal compatible with an ordinary television signal scanning mode (raster conversion).

The image processor 13 performs various processing required including gradation processing on the B mode image signal entered from the DSC 12 to produce and store two-dimensional image data in the image memory 16 while it also produces three-dimensional image data from the two-dimensional image data stored in the image memory 16 and produces outputs three-dimensional image data to the display controller 14.

The signal processor 11, the DSC 12, the image processor 13, and the image memory 16 constitute an image producer 20.

The display controller 14 causes the monitor 15 to display a three-dimensional ultrasound diagnostic image based on the three-dimensional image data entered from the image processor 13.

The monitor 15 includes a display device such as an LCD, for example, and displays an ultrasound diagnostic image under the control of the display controller 14.

The apparatus body controller 17 controls the components in the ultrasound diagnostic apparatus according to the instructions entered by the operator using the operating unit 18. The apparatus body controller 17 controls the transmission circuit 5 and the reception circuit 6 via the probe controller 7 so as to perform one of a normal scan and a composite scan. In the normal scan, the ultrasonic beams are transmitted and received evenly for the whole area of an observation space region including the region of interest according to the internal temperature Tp detected by the temperature sensor 8 of the ultrasound probe 1. In the composite scan, two different temperature rise suppression type scans are performed alternately.

The operating unit 18, provided for the operator to perform input operations, constitutes a region-of-interest setting unit in the present invention and may be composed of, for example, a keyboard, a mouse, a track ball, and/or a touch panel.

The storage unit 19 stores an operation program or the like, and a recording medium such as a hard disk, a flexible disk, an MO, an MT, a RAM, a CD-ROM, a DVD-ROM, an SD card, a CF card, or a USB memory, a server, or the like may be used.

The signal processor 11, the DSC 12, the image processor 13, the display controller 14, and the apparatus body controller 17 are each constituted by a CPU and an operation program for causing the CPU to perform various kinds of processing; they may be each constituted by a digital circuit.

To produce a three-dimensional image, the transmission circuit 5 and the reception circuit 6 operate the transducer array 3 to electronically scan the object with the ultrasonic beams to obtain two-dimensional image data in one tomographic plane, while the array moving unit 4 causes the transducer array 3 to mechanically scan the object, thereby gathering two-dimensional image data corresponding to a number of tomographic planes.

Specifically, a plurality of ultrasound transducers of the transducer array 3 transmit ultrasonic waves according to the actuation signals supplied from the transmission circuit 5 of the ultrasound probe 1, and the ultrasound transducers having received ultrasonic echoes from the subject output the reception signals to the reception circuit 6, which produces the reception data. The signal processor 11 of the diagnostic apparatus body 2 having received the reception data produces the B mode image signal, and the DSC 12 performs raster conversion of the B mode image signal, while the image processor 13 performs various image processing on the B mode image signal. Thus, two-dimensional image data for one tomographic plane are produced and stored in the image memory 16.

Thus, as two-dimensional image data for one tomographic plane are produced, the array moving unit 4 operates the transducer array 3 to mechanically scan the subject in a given angular range or with a given stroke to sequentially produce two-dimensional image data corresponding to a number of tomographic planes, which image data are stored in the image memory 16. Using the image data stored in the image memory 16, the image processor 13 produces three-dimensional image data for a space defined by the range of the electronic scan and the angular range or the stroke of the mechanical scan by the transducer array 3. Based on the three-dimensional image data, the display controller 14 displays a three-dimensional image on the monitor 15 by an image projection method such as, for example, the VR (Volume Rendering) or the MPR (Multiplanar Reconstruction).

Figure 2:
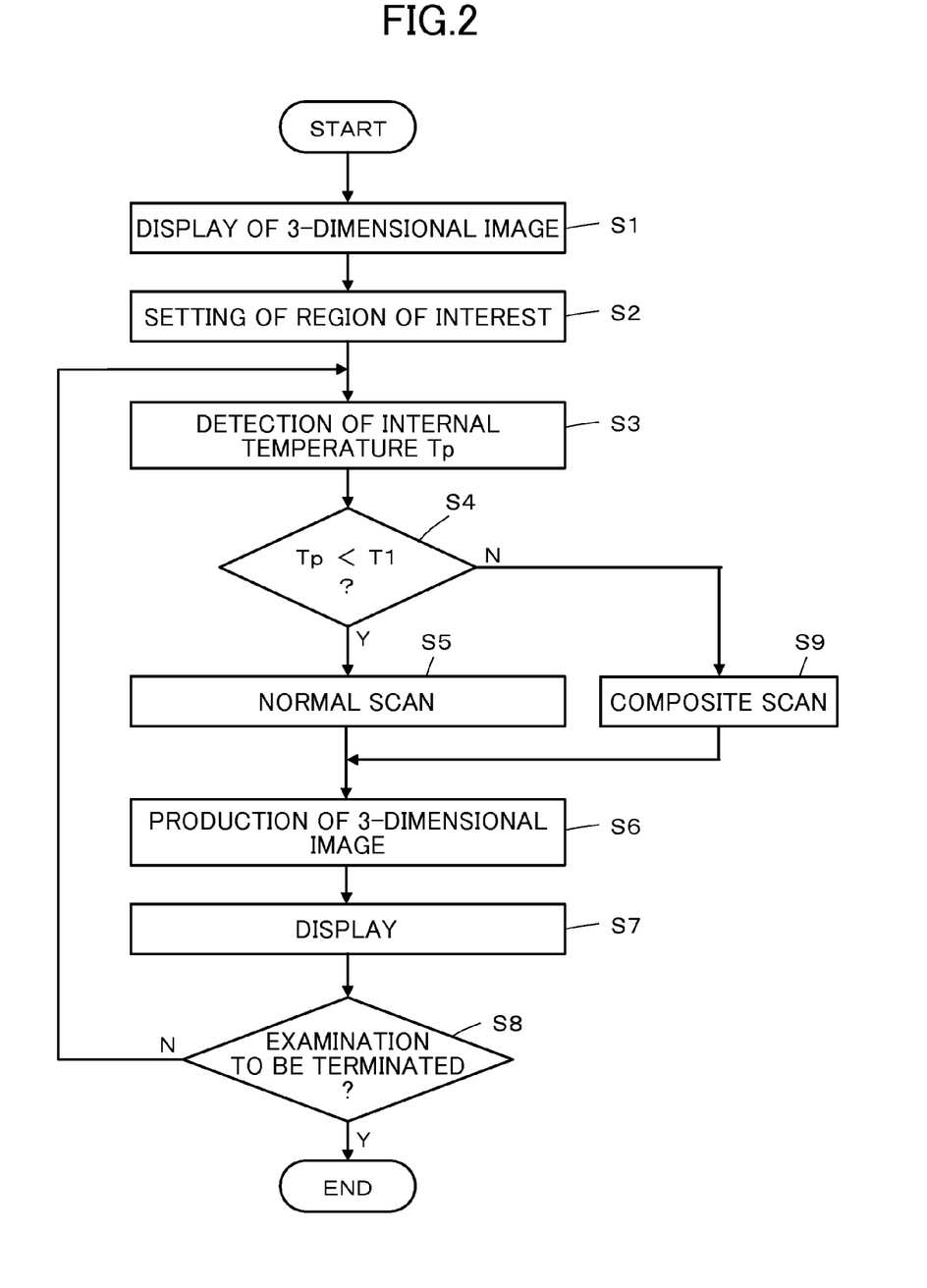
FIG. 2 is a flowchart illustrating the operation of Embodiment 1.

Next, the operation of Embodiment 1 will be described referring to the flowchart of FIG. 2.

First, in step S1, the transmission circuit 5 and the reception circuit 6 operate the transducer array 3 to electronically scan the subject and obtain two-dimensional image data, while the array moving unit 4 operates the transducer array 3 to mechanically scan the subject to produce three-dimensional image data, whereupon the display controller 14 displays the three-dimensional image on the monitor 15.

Figure 3:
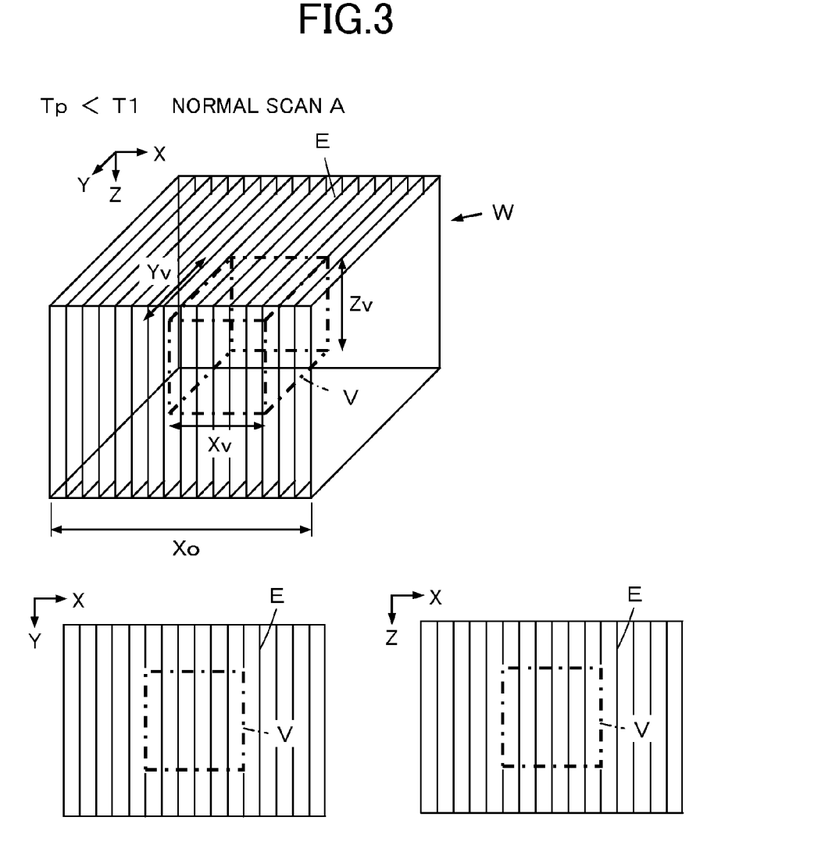
FIG. 3 is a diagram showing a scan method with a transducer array when the internal temperature of an ultrasound probe is below a first set value in Embodiment 1.

In step S2, the operator operates the operating unit 18 to set a region of interest V in a three-dimensional image of an observation space region W displayed on the monitor 15 as illustrated in FIG. 3. In FIG. 3, the array moving unit 4 causes the transducer array 3 to reciprocate in linear motion with a stroke of Xo, for example. The X-axis shows the movement direction of the transducer array 3 actuated by the array moving unit 4, i.e., mechanical scan direction; the Y-axis shows the one-dimensional array direction of the ultrasound transducers of the transducer array; and the Z-axis shows the measuring depth direction. The region of interest V has a length of Xv, Yv, and Zv in the directions of X-axis, Y-axis, and Z-axis, respectively.

With the region of interest V thus determined, the temperature sensor 8 detects the internal temperature Tp of the ultrasound probe 1 in step S3, and the detected internal temperature Tp is compared with a predetermined first set value T1 in step S4.

Figure 4:
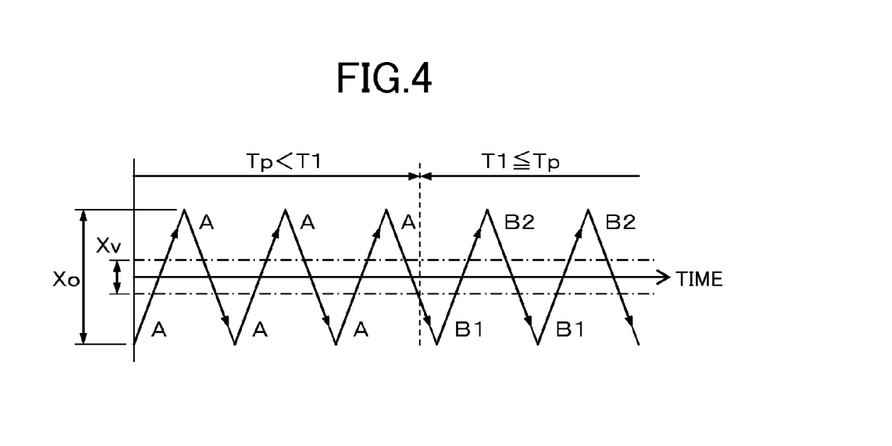
FIG. 4 is a timing chart illustrates a switching of scan methods with the transducer array in Embodiment 1.

When the internal temperature Tp of the ultrasound probe 1 is judged to be below the first set value T1, the procedure proceeds to step S5, where the apparatus body controller 17 controls the reception circuit 6 via the probe controller 7 to perform the normal scan A. Specifically, as illustrated in FIG. 3, the transmission circuit 5 and the reception circuit 6 causes the transducer array 3 to electronically scan the subject as the array moving unit 4 operates the transducer array 3 to mechanically scan the subject to form an electronic scan plane E evenly over the whole area of the observation space region W regardless of the region of interest V and produce two-dimensional image data for the respective electronic scan planes E, which image data are stored in the image memory 16. So long as the internal temperature Tp of the ultrasound probe 1 remains below the first set value T1 as illustrated in FIG. 4, the transducer array 3 performs the normal scan A in the backward and the forward movement of its reciprocating motion.

Next, in step S6, the image processor 13 uses the two-dimensional image data stored in the image memory 16 to produce three-dimensional image data for the observation space region W; in the following step S7, the display controller 14 displays the three-dimensional image on the monitor 15.

In step S8, whether the examination is to be terminated is determined, and when the examination is to be continued, the steps S3 to S8 are repeated; when the examination is to be terminated, the sequential processing are terminated.

While the ultrasound diagnosis is thus carried out, the internal temperature Tp of the ultrasound probe 1 may gradually increase with the passage of time as the procedure proceeds. When the internal temperature Tp of the ultrasound probe 1 is judged in step S4 to have reached or exceeded the first set value T1, the procedure proceeds to step S9, where the apparatus body controller 17 controls the transmission circuit 5 and the reception circuit 6 via the probe controller 7 to perform the composite scan.

As illustrated in FIG. 4, the composite scan includes a temperature rise suppression type scan B1 performed in the forward movement of the reciprocating motion of the transducer array 3 and a temperature rise suppression type scan B2 performed in the backward movement. The temperature rise suppression type scans B1 and B2 are different in details of scan and performed alternately as the transducer array 3 makes its reciprocating motion.

Figure 5:
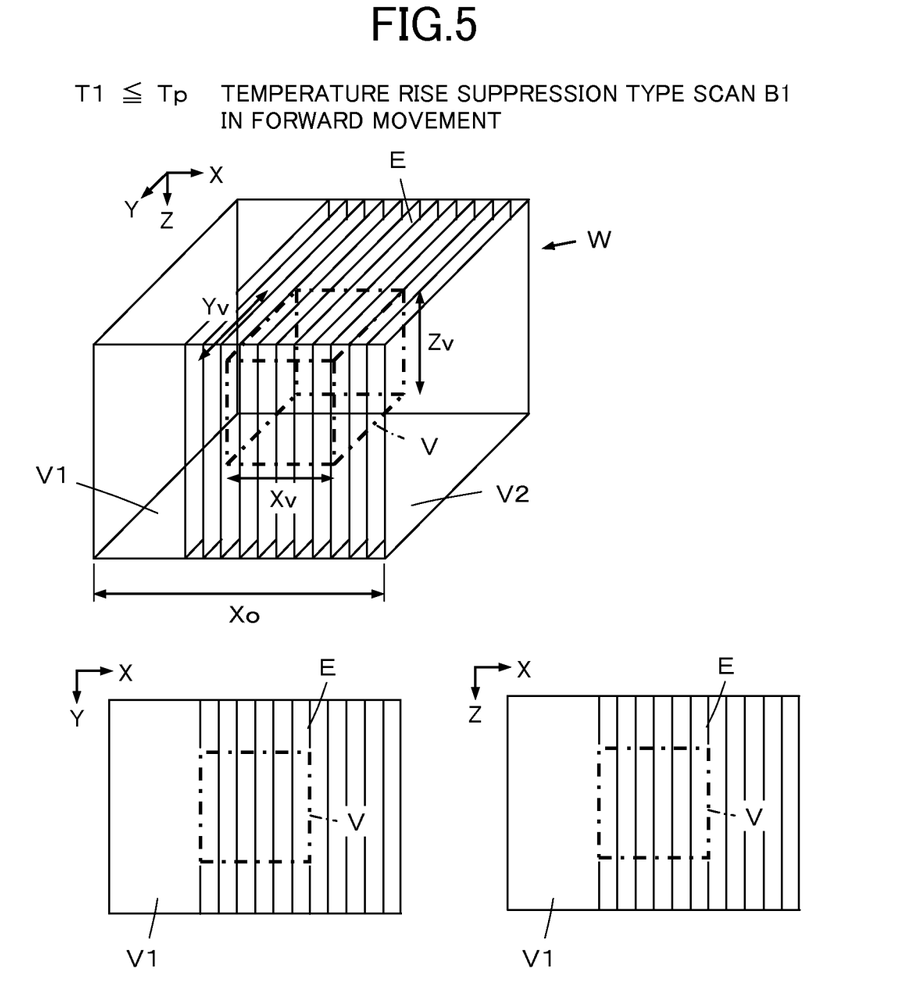
FIG. 5 is a diagram showing a scan method in a forward movement of a reciprocating back and forth motion of the transducer array when the internal temperature of the ultrasound probe has reached or exceeded the first set value in Embodiment 1.

In the temperature rise suppression type scan B1 performed in the forward movement, the array moving unit 4 operates the transducer array 3 to perform the mechanical scan over the whole area of the observation space region W regardless of the region of interest V as illustrated in FIG. 5. In the mechanical scan direction of the transducer array 3, or the X-axis direction, the transmission and reception of the ultrasonic beams are paused for a first region V1 among the region other than the region of interest V including the first region V1 and a second region V2, the region V1 being located on the side of the region of interest V in the minus X direction and the region V2 being located on the side of the region of interest V in the plus X direction, so that the electronic scan plane E is formed only in a region containing the region of interest V and the second region V2 located on the side of the region of interest V in the plus X direction.

Figure 6:
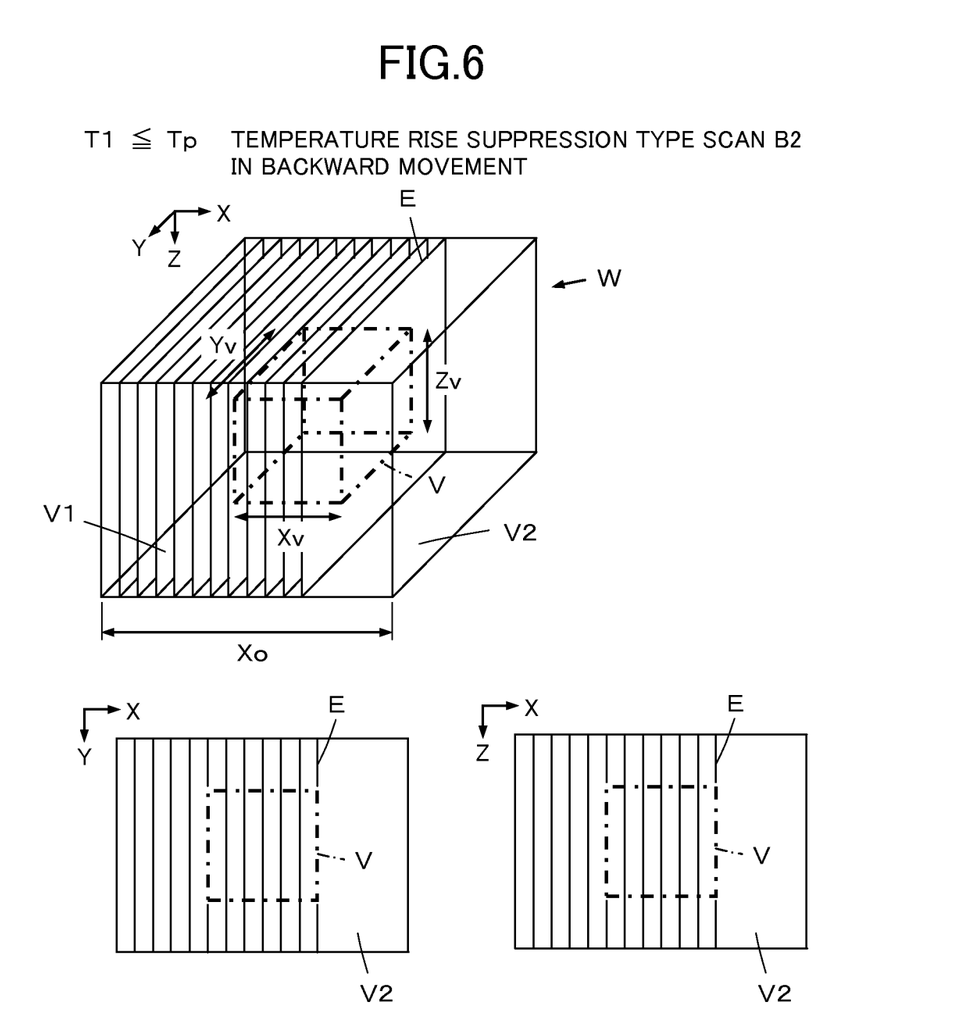
FIG. 6 is a diagram showing a scan method in a backward movement of the reciprocating motion of the transducer array when the internal temperature of the ultrasound probe has reached or exceed the first set value in Embodiment 1.

In the temperature rise suppression type scan B2 performed in the backward movement, the array moving unit 4 operates the transducer array 3 to perform the mechanical scan over the whole area of the observation space region W regardless of the region of interest V as illustrated in FIG. 6. In the mechanical scan direction of the transducer array 3, or the X-axis direction, the transmission and reception of the ultrasonic beams are paused for the second region V2 among the region other than the region of interest V including the first region V1 and the second region V2, so that the electronic scan plane E is formed only in a region containing the region of interest V and the first region V1 located on the side of the region of interest V in the minus X direction.

Thus, in the forward movement of the reciprocating motion of the transducer array 3, the transmission and reception of the ultrasonic beams are paused for the first region V1 whereas, in the backward movement, the transmission and reception of the ultrasonic beams are paused for the second region V2, so that the operation of the transmission circuit 5 and the reception circuit 6 is paused for the longer time period, thereby suppressing the temperature rise inside the ultrasound probe 1.

Next, in step S6, the image processor 13 uses the two-dimensional image data for the electronic scan plans E stored in the image memory 16 to produce three-dimensional image data, and in the following step S7, the display controller 14 displays the three-dimensional image on the monitor 15.

With these temperature rise suppression type scans, when the internal temperature Tp of the ultrasound probe 1 decreases to the first set value T1 or lower, the normal scan is resumed to display the three-dimensional image.

In the forward movement of the reciprocating motion of the transducer array 3, for example, the electronic scan plane E is not formed for the first region V1 outside the region of interest V, but a three-dimensional image for the whole region of the observation space region W can be displayed by using the electronic scan plane E for the first region V1 formed in the backward movement of the preceding reciprocating motion Likewise, in the backward movement of the reciprocating motion of the transducer array 3, for example, the electronic scan plane E is not formed for the second region V2 outside the region of interest V, but a three-dimensional image for the whole region of the observation space region W can be displayed by using the electronic scan plane E for the second region V2 formed in the forward movement of the preceding reciprocating motion.

As described above, when the internal temperature Tp of the ultrasound probe 1 detected by the temperature sensor 8 has reached or exceeded the first set value T1, the transmission circuit 5 and the reception circuit 6 are controlled to perform the composite scan including the temperature rise suppression type scans B1 and B2, so that a high-quality three-dimensional ultrasound image can be obtained at least for the region of interest V while suppressing the increase in the internal temperature Tp of the ultrasound probe 1.

Embodiment 2

Although, according to Embodiment 1, the temperature rise suppression type scans B1 and B2 are performed alternately as the composite scan when the internal temperature T of the ultrasound probe 1 has reached or exceeded the first set value T1, the composite scan consisting of the temperature rise suppression type scan may be performed alternately with the normal scan A that is performed when the internal temperature Tp of the ultrasound probe 1 is below the first set value T1.

Figure 7:
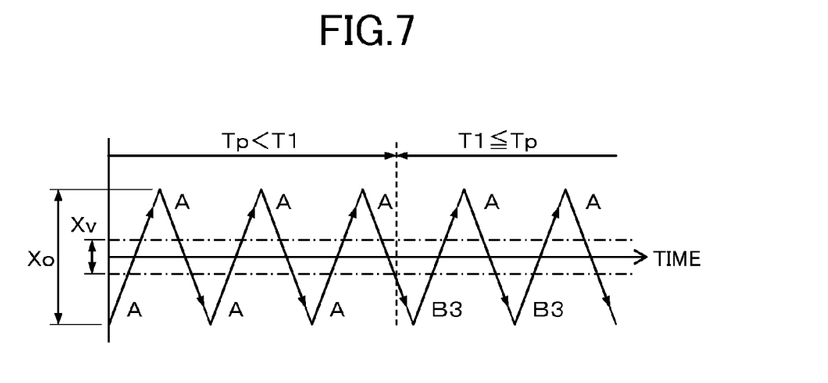
FIG. 7 is a timing chart illustrates a switching of scan methods with the transducer array in Embodiment 2.

When, for example, the internal temperature Tp of the ultrasound probe 1 has reached or exceeded the first set value T1, a temperature rise suppression type scan B3 may be performed in the forward movement of the reciprocation motion of the transducer array 3 as illustrated in FIG. 7, whereas the normal scan A may be performed in the backward movement as illustrated in FIG. 3.

Figure 8:
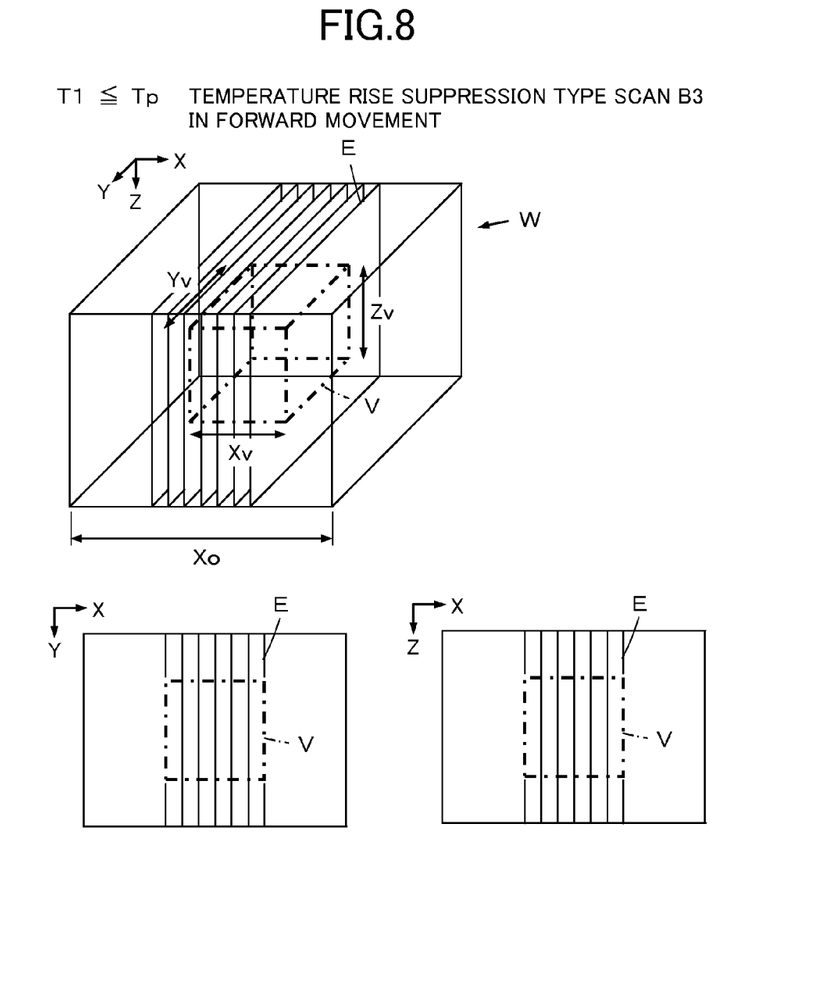
FIG. 8 is a diagram showing a scan method in a forward movement of a reciprocating motion of the transducer array when the internal temperature of the ultrasound probe has reached or exceeded the first set value in Embodiment 2.

In the temperature rise suppression type scan B3 performed in the forward movement, the array moving unit 4 operates the transducer array 3 to perform the mechanical scan over the whole area of the observation space region W regardless of the region of interest V as illustrated in FIG. 8. In the mechanical scan direction of the transducer array 3, or the X-axis direction, the electronic scan plane E is formed only for a range in which the region of interest E lies, and the transmission and reception of the ultrasonic beams are paused for the region other than the region of interest V as seen in the X-axis direction. Thus, the operation of the transmission circuit 5 and the reception circuit 6 is paused for a period of time increased accordingly, and the rise in the internal temperature inside the ultrasound probe 1 can be suppressed.

Such composite scan also enables acquisition of a high-quality three-dimensional ultrasound image for at least the region of interest V while suppressing the increase in the internal temperature Tp of the ultrasound probe 1.

Embodiment 3

According to Embodiments 1 and 2, the first set value T1 is provided, and the composite scan is performed when the internal temperature Tp of the ultrasound probe 1 has reached or exceeded the first set value T1, but a plurality of set values may be provided to enable a step-wise composite scan to be performed whereby the effects of temperature rise suppression differ according to the internal temperature Tp of the ultrasound probe 1.

Figure 9:
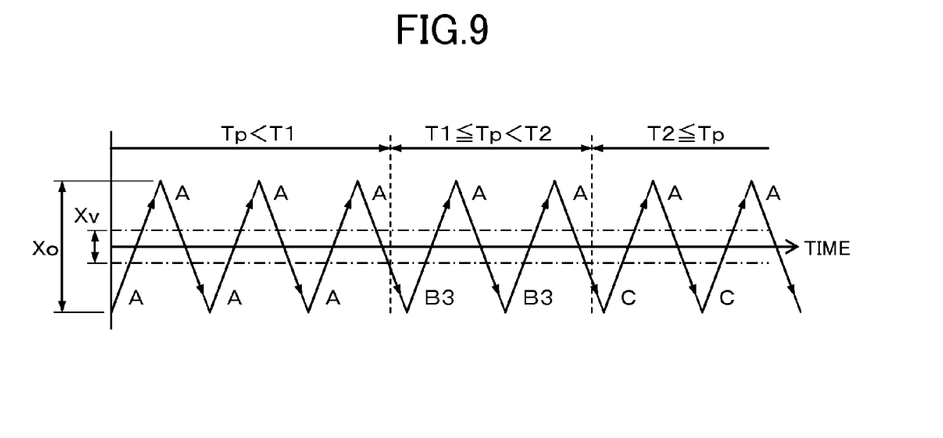
FIG. 9 is a timing chart illustrates a switching of scan methods with the transducer array in Embodiment 3.

For example, with a second set value T2 provided in addition to the first set value T1 so that T2 is higher than T1 as illustrated in FIG. 9, the normal scan A illustrated in FIG. 3 is performed in both the backward and the forward movement of the reciprocating motion of the transducer array 3 when the internal temperature Tp of the ultrasound probe 1 is below the set value T1, as according to Embodiment 2; the temperature rise suppression type scan B3 illustrated in FIG. 8 is performed in the forward movement of the reciprocating motion of the transducer array 3 while the normal scan A is performed in the backward movement when the internal temperature Tp of the ultrasound probe 1 has reached or exceeded the set value T1 and is below the second set value T2; and another temperature rise suppression type scan C is performed in the forward movement of the reciprocating motion of the transducer array 3 while the normal scan A is performed in the backward movement when the internal temperature Tp of the ultrasound probe 1 has reached or exceeded the second set value T2.

Figure 10:
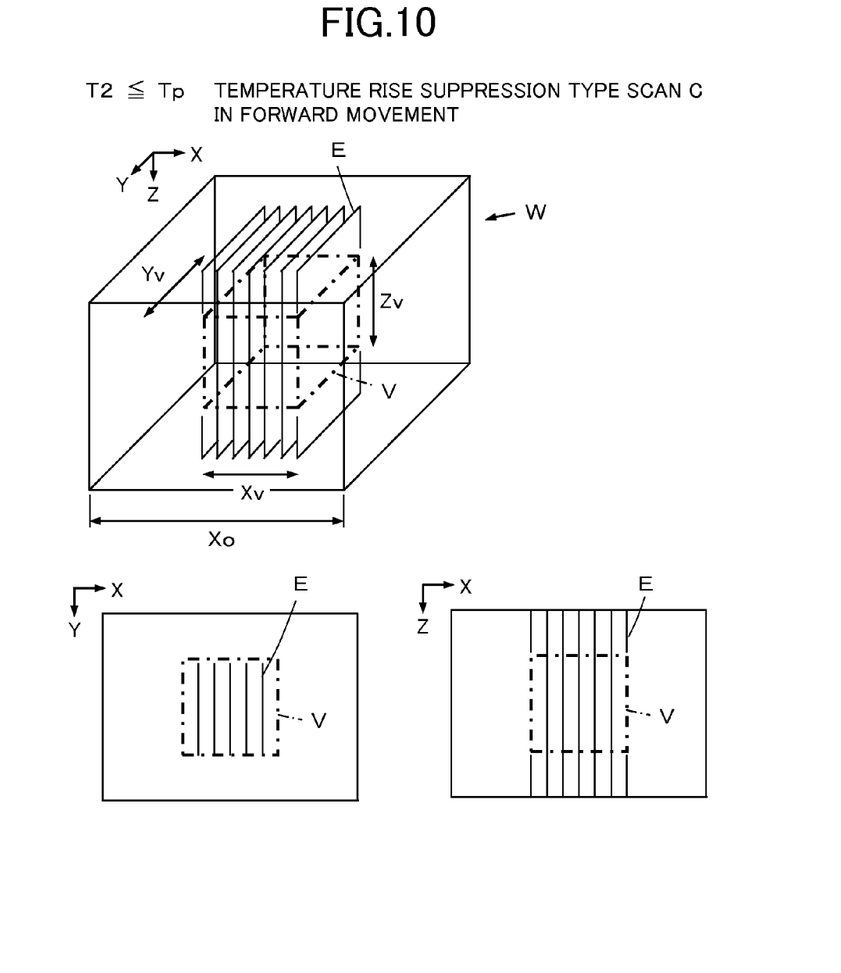
FIG. 10 is a diagram showing a scan method in a forward movement of a reciprocating motion of the transducer array when the internal temperature of the ultrasound probe has reached or exceeded a second set value in Embodiment 3.

As illustrated in FIG. 10, in the temperature rise suppression type scan C, the electronic scan plane E is formed not only for only a range defined by the length Xv in which the region of interest V lies in the direction of the mechanical scan by the transducer array 3, but for only a range defined by the length Yv in which the region of interest V lies in the Y-axis direction or the one-dimensional array direction of the transducer array 3, so that the transmission and the reception of the ultrasonic beams are paused for the region other than the region of interest V as seen in the Y-axis direction.

In the temperature rise suppression type scan C, the range in which the transmission and the reception of the ultrasonic beams are paused increases by the region other than the region of interest V in the Y-axis direction as compared with the temperature rise suppression type scan B3 performed when the internal temperature Tp of the ultrasound probe 1 has reached or exceeded the set value T1 and is below the second set value T2, and the operation of the transmission circuit 5 and the reception circuit 6 is paused for a period increased accordingly, resulting in the suppression of the rise in the internal temperature inside the ultrasound probe 1.

Further, with a third set value T3 provided so that T3 is higher than T2, when the internal temperature Tp detected by the temperature sensor 8 of the ultrasound probe 1 has reached or exceeded the third set value T3, the electronic scan plane E may be formed for a range Zv where the region of interest V lies and a region shallower than the region of interest V as seen in the Z-axis direction or the measuring depth direction, to discontinue the reception of the ultrasonic beams for the region deeper than the region of interest V.

According to Embodiments 2 and 3, the electronic scan plane E is not formed for a part of the region other than the region of interest V in the forward movement of the reciprocating motion of the transducer array 3, while the electronic scan plane E is formed for the whole observation space region W as the normal scan A is performed in the backward movement. Using the electronic scan plane E formed in the backward movement of the preceding reciprocating motion, a three-dimensional image for the whole region of the observation space region W can be displayed also in the forward movement.

According to Embodiments 1 to 3, while the transmission and reception of the ultrasonic beams are paused in the temperature rise suppression type scans B1, B2, B3, and C for at least a part of the region other than the region of interest V in the X-axis direction or the direction of the mechanical scan by the transducer array 3, the invention is not limited thereto. The reception of the ultrasonic beams may be paused for at least a part of the region other than the region of interest V as seen in the Y-axis direction or the one-dimensional array direction of the transducer array 3, or for at least a part of the region other than the region of interest V as seen in the Z-axis direction or the measuring depth direction.

Further, the transmission circuit 5 and the reception circuit 6 can also be paused for an increased time period, and a high-quality three-dimensional image can be obtained at least for the region of interest V while suppressing the rise in the internal temperature Tp of the ultrasound probe 1 as according to Embodiments 1 to 3 by a scan whereby the ultrasonic beams are transmitted and received intermittently for at least a part of the region other than the region of interest V or by the composite scan including the temperature rise suppression type scan whereby the ultrasonic beams are transmitted and received or only received, with a decreased spacial resolution for at least a part of the region other than the region of interest V instead of discontinuing the transmission and reception of the ultrasonic beams for at least a part of the region other than the region of interest V.

According to Embodiments 1 to 3, while the array moving unit 4 causes the transducer array 3 to make a linear reciprocating motion with the stroke of Xo, the transducer array may be allowed to vibrate in a direction substantially perpendicular to the array direction of the ultrasound transducers.

The connection between the ultrasound probe 1 and the diagnostic apparatus body 2 according to Embodiments 1 to 3 may be achieved by wired communication or wireless communication.

What is claimed is:

1. An ultrasound diagnostic apparatus comprising:
an ultrasound probe which has a one-dimensional array type transducer array and an array moving unit moving the one-dimensional array type transducer array in a direction substantially perpendicular to an array direction of the one-dimensional array type transducer array;
a transmission and reception circuit which electronically scans with the one-dimensional array type transducer array, and transmits and receives an ultrasonic beam toward a subject to acquire two-dimensional image data;
an image producer which produces a three-dimensional ultrasound image using two-dimensional image data acquired by the transmission and reception circuit while mechanically scanning with the one-dimensional array type transducer array in a direction substantially orthogonal to the array direction of the one-dimensional array type transducer array by the array moving unit;
a region of interest setter which sets a region of interest in an imaging region;
a temperature sensor which detects an internal temperature of the ultrasound probe; and
a controller which, when the internal temperature of the ultrasound probe detected by the temperature sensor is equal to or higher than a first set value, controls the transmission and reception circuit such that a composite scan including two different electronic scans being repeated alternately is performed,
each of the two different electronic scans being a scan in which transmission and reception of ultrasonic beams for the region of interest set by the region of interest setter are performed as same as when the internal temperature of the ultrasound probe detected by the temperature sensor is below the first set value, and
at least one of the two different electronic scans being a temperature rise suppression type scan in which transmission and reception of ultrasonic beams or reception of ultrasonic beams for at least a part of a region other than the region of interest set by the region of interest setter are paused for a longer time period than those when the internal temperature of the ultrasound probe detected by the temperature sensor is below the first set value.

2. The ultrasound diagnostic apparatus according to claim 1, wherein the temperature rise suppression type scan is at least one of
a scan in which transmission and reception of ultrasonic beams or reception of ultrasonic beams for at least a part of a region other than the region of interest is paused,
a scan in which transmission and reception of ultrasonic beams or reception of ultrasonic beams for at least a part of the region other than the region of interest is intermittently performed, and
a scan in which transmission and reception of ultrasonic beams or reception of ultrasonic beams for at least a part of the region other than the region of interest is performed with a decreased spacial resolution.

3. The ultrasound diagnostic apparatus according to claim 2, wherein in the composite scan, the two different electronic scans composed of the temperature rise suppression type scans are performed alternately.

4. The ultrasound diagnostic apparatus according to claim 3, wherein the two different electronic scans are composed of
a scan in which transmission and reception of ultrasonic beams for one part of the region other than the region of interest in a direction of mechanical scan with the one-dimensional array type transducer array are paused, and
a scan in which transmission and reception of ultrasonic beams for another part of the region other than the region of interest in the direction of mechanical scan with the one-dimensional array type transducer array are paused.

5. The ultrasound diagnostic apparatus according to claim 2, wherein in the composite scan, the two different electronic scans including the temperature rise suppression type scan and a scan performed when the internal temperature of the ultrasound probe detected by the temperature sensor is below the first set value are performed alternately.

6. The ultrasound diagnostic apparatus according to claim 5, wherein the temperature rise suppression type scan is a scan in which transmission and reception of ultrasonic beams are paused for the region other than the region of interest in the direction of mechanical scan with the one-dimensional array type transducer array.

7. The ultrasound diagnostic apparatus according to claim 6, wherein, when the internal temperature of the ultrasound probe detected by the temperature sensor is equal to or higher than a second set value which is set to be higher than the first set value, the controller controls the transmission and reception circuit such that a scan is further performed, as the temperature rise suppression type scan, in which transmission and reception of ultrasonic beams for the region other than the region of interest in the array direction of the one-dimensional array type transducer array is paused.

8. A method of producing an ultrasound image, the method comprising the steps of:
setting a region of interest in an imaging region;
detecting an internal temperature of an ultrasound probe;
electronically scanning with a one-dimensional array type transducer array of the ultrasound probe by a transmission and reception circuit and transmitting and receiving ultrasonic beams toward a subject to acquire two-dimensional image data, and mechanically scanning with the one-dimensional array type transducer array in a direction substantially orthogonal to an array direction of the one-dimensional array type transducer array to acquire a plurality of pieces of two-dimensional image data;
producing a three-dimensional ultrasound image using a plurality of pieces of acquired two-dimensional image data; and
when a detected internal temperature of the ultrasound probe is equal to or higher than a first set value, controlling the transmission and reception circuit such that a composite scan including two different electronic scans being repeated alternately is performed,
wherein each of the two different electronic scans being a scan in which transmission and reception of ultrasonic beams for the region of interest set are performed as same as when the internal temperature detected of the ultrasound probe is below the first set value, and
at least one of the two different electronic scans is a temperature rise suppression type scan in which transmission and reception of ultrasonic beams or reception of ultrasonic beams for at least a part of a region other than the region of interest set are paused for a longer time period than those when the detected internal temperature of the ultrasound probe is below the first set value.

* * * * *